United States Patent
Miller et al.

(10) Patent No.: US 8,331,529 B2
(45) Date of Patent: Dec. 11, 2012

(54) X-RAY BEAM Z-AXIS POSITIONING

(75) Inventors: Lester Miller, Hudson, OH (US);
Janardhan K. Kamath, Solon, OH (US); Randall P. Luhta, Highland Heights, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 598 days.

(21) Appl. No.: 12/597,178

(22) PCT Filed: Mar. 28, 2008

(86) PCT No.: PCT/IB2008/051175
§ 371 (c)(1),
(2), (4) Date: Oct. 23, 2009

(87) PCT Pub. No.: WO2008/132635
PCT Pub. Date: Nov. 6, 2008

(65) Prior Publication Data
US 2010/0119039 A1 May 13, 2010

Related U.S. Application Data (60) Provisional application No. 60/913,831, filed on Apr. 25, 2007.

(51) Int. Cl.
*G01N 23/04* (2006.01)
(52) U.S. Cl. .............................. 378/62; 378/147; 378/93
(58) Field of Classification Search .................... 378/62, 378/147–153, 93
See application file for complete search history.

(56) References Cited

U.S. PATENT DOCUMENTS

| | | | |
|---|---|---|---|
| 4,837,792 A | 6/1989 | Goethert | |
| 4,991,189 A | 2/1991 | Boomgaarden et al. | |
| 5,469,429 A | 11/1995 | Yamazaki et al. | |
| 5,566,220 A | 10/1996 | Saito et al. | |
| 5,684,855 A | 11/1997 | Aradate et al. | |
| 6,185,275 B1 * | 2/2001 | Toth et al. ...................... | 378/113 |
| 6,215,844 B1 | 4/2001 | Adachi et al. | |
| 6,322,248 B1 | 11/2001 | Yanagita et al. | |
| 2005/0094762 A1 | 5/2005 | Dunham et al. | |
| 2005/0243969 A1 | 11/2005 | Andrews | |

FOREIGN PATENT DOCUMENTS

| | | |
|---|---|---|
| EP | 1078599 A1 | 2/2001 |
| EP | 1121899 A1 | 8/2001 |

* cited by examiner

*Primary Examiner* — Irakli Kiknadze (57) ABSTRACT

A medical imaging system includes an x-ray source (112) having a focal spot that emits radiation that traverses an examination region (108). The position of the focal spot along a longitudinal direction is a function of a temperature of one or more x-ray source components. The system further includes a detector (120) that detects the radiation and a collimator (116), disposed between the x-ray source (112) and the examination region (108), that collimates that radiation along the longitudinal direction. A focal spot position estimator (132) dynamically computes an estimated position of the focal spot along the longitudinal direction based on the temperature of one or more x-ray source components. A collimator positioner (128) positions the collimator (116) along the longitudinal direction based on the estimated focal spot position prior to performing a scan.

24 Claims, 7 Drawing Sheets

X-RAY BEAM Z-AXIS POSITIONING

CROSS REFERENCE TO RELATED APPLICATIONS

This application claims the benefit of U.S. provisional application Ser. No. 60/913,831 filed Apr. 25, 2007, which is incorporated herein by reference.

The present application generally relates to imaging. While it finds particular application to computed tomography (CT), it also relates to other imaging applications in which it is desirable to selectively position a radiation beam along an axis.

Computed tomography (CT) systems have included an x-ray tube that emits radiation that traverses an examination region and a detector that detects the radiation. The detector generates a signal indicative of the detected radiation, and the signal is reconstructed to generate volumetric image data indicative of the examination region.

The x-ray tube has included a cathode and an anode. The cathode has included a filament that provides electrons that are accelerated towards and strike a target region on an anode under relatively high voltage. The interaction of the electrons with the anode material at the target region produces radiation that is emitted from the target region. The target region has been referred to as the focal spot.

A collimator has been used to collimate the emitted radiation so that a radiation beam traverses the examination region. It has been desirable to collimate the emitted radiation along a longitudinal or z-axis so that a z-axis width of the radiation beam at the detection surface of the detector corresponds to about a z-axis width of the detection surface since radiation outside of this region is not detected and, hence, does not contribute to the volumetric image data. Such undetected radiation leads to inefficient utilization of the radiation and may contribute to the aggregate dose received by the patient or other object under examination.

Unfortunately, during x-ray generation the interaction of the accelerated electrons with the anode also produces heat. This heat dissipates from the anode as well as other components and materials in thermal communication with the anode such as the stem that supports the anode, the bearings that support the stem, cooling fluid that circulates around an enclosure enclosing the anode, stem and bearings, and the x-ray tube housing. As a consequence, the physical dimensions of the anode, stem, bearings and other components of the x-ray tube may change as they absorb and dissipate heat. As a result, the focal spot may move along the z-axis, and such movement has caused the radiation beam at the detection surface to move so that the beam no longer illuminates the detection surface as desired. For instance, the radiation beam has moved so that portions of the detection surface no longer receive radiation.

To compensate for such thermally induced focal spot movement, the size of the collimator aperture has been increased along the z-axis so that the width of the radiation beam illuminating the detection surface is greater than the width of the detection surface. The aperture width has been configured so that the radiation beam illuminates the detection surface as the focal spot moves over the operating temperature range of the x-ray tube. However, and as noted above, only detected radiation contributes to the volumetric image data so this technique introduces radiation utilization and dose inefficiencies.

Another compensation technique includes processing detected radiation while scanning to determine if there is a z-axis radiation detection imbalance along the detection surface, which is indicative of focal spot movement. When an imbalance is detected, the collimator has been re-positioned so that the radiation beam is again balanced and illuminates the desired region of detection surface. Unfortunately, this technique requires detected radiation. As a consequence, the collimator may not be in the desired position when a scan begins. Thus, the radiation traversing the examination region during an initial time interval after a scan commences may not be used to generate the volumetric image data and, therefore, this technique leads to radiation utilization and dose inefficiencies.

Aspects of the present application address the above-referenced matters and others.

According to one aspect, a medical imaging system includes an x-ray source having a focal spot that emits radiation that traverses an examination region. The position of the focal spot along a longitudinal direction is a function of a temperature of one or more x-ray source components. The system further includes a detector that detects the radiation and a collimator, disposed between the x-ray source and the examination region, that collimates that radiation along the longitudinal direction. A focal spot position estimator dynamically computes an estimated position of the focal spot along the longitudinal direction based on the temperature of one or more x-ray source components. A collimator positioner positions the collimator along the longitudinal direction based on the estimated focal spot position prior to performing a scan.

According to another aspect, a method includes estimating a temperature of one or more components in thermal communication with an anode of an imaging system, computing an estimated z-axis position of the anode based on the temperature, and pre-positioning the collimator along the z-axis based on the estimated anode position before performing a scan.

A computer readable storage medium containing instructions which, when executed, cause a computer to carry out the steps of positioning a collimator along a longitudinal direction prior to performing a scan based on a computed estimated position of a radiation beam.

Still further aspects of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
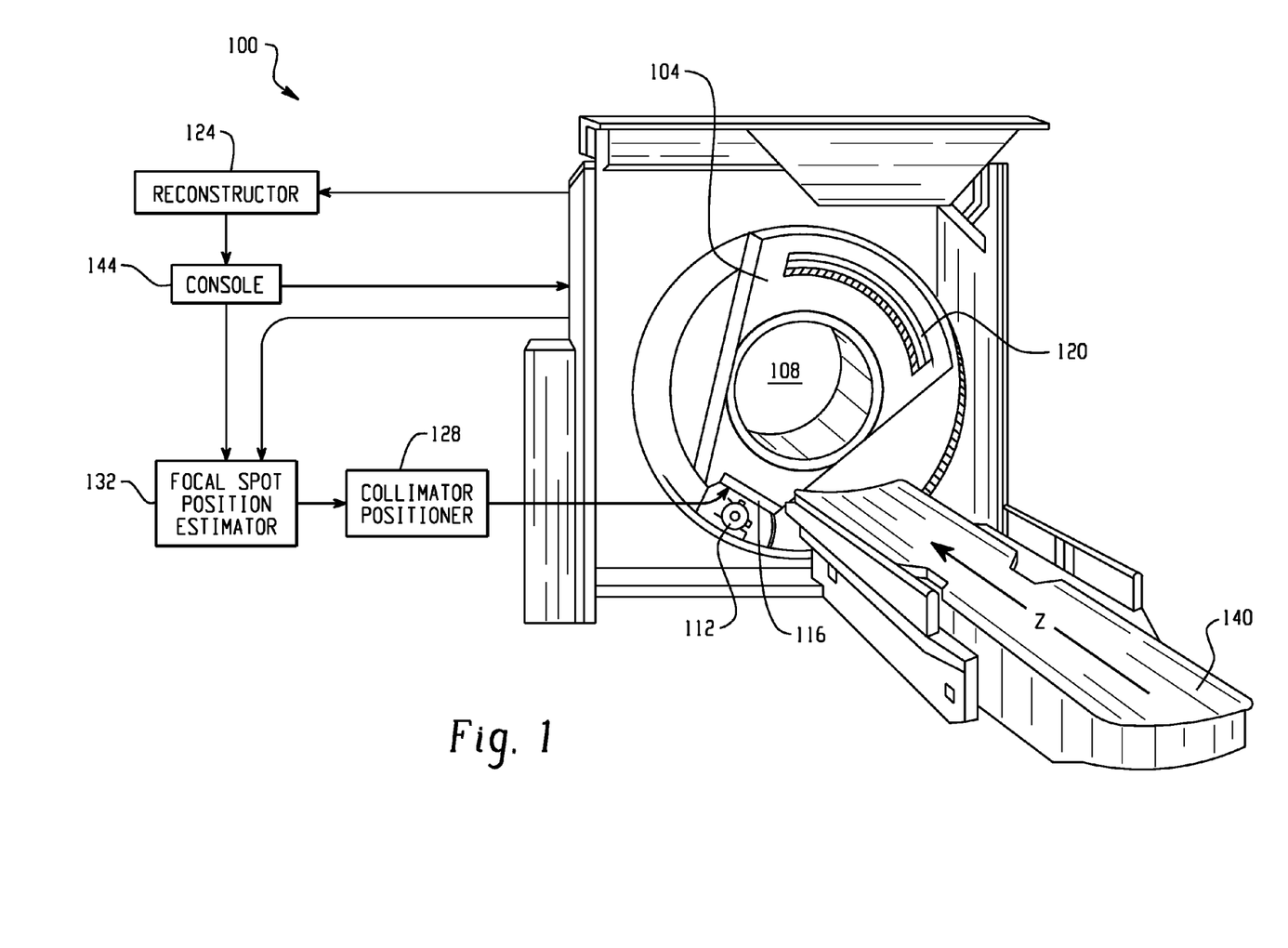
FIG. 1 illustrates an imaging system.

With reference to FIG. 1, a computed tomography (CT) scanner 100 includes a rotating gantry portion 104 that rotates about an examination region 108 around a longitudinal or z-axis. The rotating gantry portion 104 supports an x-ray source 112 that emits x-rays from a focal spot, or target region on an anode (not visible) of the x-ray source 112. The rotating gantry portion 104 also supports a collimator 116, disposed between the x-ray source 112 and the examination region 108, that collimates the emitted radiation along the z-axis to form a radiation beam that traverses the examination region 108.

The rotating gantry portion 104 also supports an x-ray detector 120 that detects radiation that traverses the examination region 108 and strikes the detector 120. The x-ray detector 120 produces projection data indicative of the detected x-rays for a plurality of projection angles with respect to the examination region 108 over one or more revolutions around the examination region 108. A reconstructor 124 reconstructs the x-ray projection data to generate volumetric image data indicative of the examination region 108.

A collimator positioner 128 selectively positions the collimator 116 along the z-axis with respect to the focal spot and the detector 120. In one instance, the collimator positioner 128 positions the collimator 116 so that the radiation beam illuminates a desired z-axis region of the detector 120. In the illustrated embodiment, the collimator positioner 128 positions the collimator 116 before and during a scan.

As discussed in greater detail below, a focal spot position estimator 132 estimates the position of the focal spot along the z-axis based on a previously determined temperature of one or more components of the x-ray source 112 such as the anode, bearings, stem, cooling fluid, or other components of the x-ray source 112. In one instance, the estimated focal spot z-axis position is processed, and the resulting signal is used by the collimator positioner 128 to position the collimator 116 before x-rays are turned on in connection with performing a scan. Such positioning may compensate for focal spot movement due to a temperature change in one or more components of the x-ray source 112.

While performing a scan, the z-axis position of the radiation beam illuminating the detector 120, along with other information such as the power applied to the x-ray source 112 and/or a previous estimated temperature of the one or more components, may be used to update the focal spot position estimator 132.

An object support 140, such as a couch, supports a patient or other object in the examination region 108. The object support 140 is movable so as to guide the patient or other subject within respect to the examination region 108 while performing a scanning procedure.

A general purpose computer serves as an operator console 144. The console 144 includes an input interface for receiving an input signal from an input device such as a keyboard or mouse. The input signal may include an instruction to activate the focal spot position estimator 132, an x-ray source parameter and/or variable for use by the focal spot position estimator 132, as well as other information. The console 144 also includes an output interface, such as a monitor, for presenting the processed data as an image in a viewport. Software resident on the console 144 interacts with the focal spot position estimator 132, including providing input to the focal spot position estimator 132.

Figure 2:
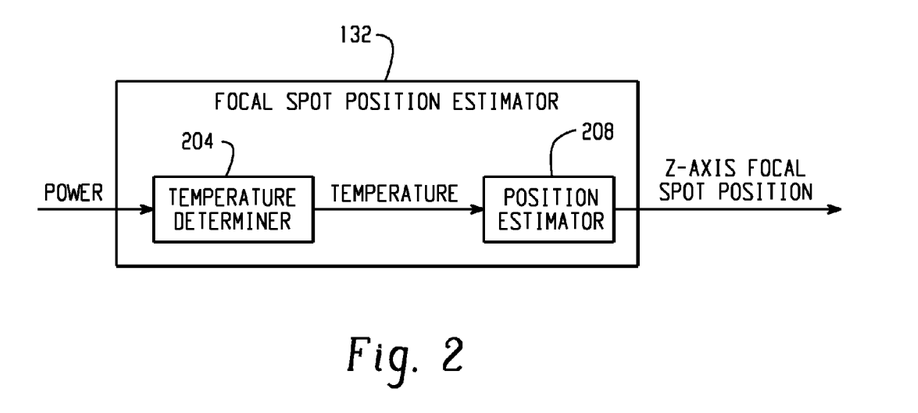
FIG. 2 illustrates a focal spot position estimator.

As noted above, the focal spot position estimator 132 estimates the position of the focal spot along the z-axis. FIG. 2 provides a block diagram of a non-limiting implementation of the focal spot position estimator 132. As illustrated in FIG. 2, the focal spot position estimator 132 includes a temperature determiner 204 and a position estimator 208 that estimates the z-axis focal spot position based on temperature determined by the temperature determiner 204.

The temperature determiner 204 uses an input such as the power applied to the x-ray source 112 to determine the temperature of one or more of the x-ray source components. In one instance, the applied power is used along with a known thermal property of one or more components of the x-ray source 112. Additionally or alternatively, a previously determined or estimated temperature of the one or more components is used to determine the temperature of the one or more components.

By way of example, the temperature determiner 204 may determine the temperature of the x-ray source anode and bearing based on the power applied to the x-ray source 112, various thermal properties of the one or more x-ray source components and/or previously determined temperatures of the anode and bearing. The temperature determiner 204 may additionally or alternatively determine a temperature of the x-ray source housing, cooling fluid, and/or other components and/or materials in thermal communication with the anode.

The position estimator 208 uses the temperature(s) determined by the temperature determiner 204 along with a known thermal property of one or more components to estimate the z-axis focal spot position.

Figure 3:
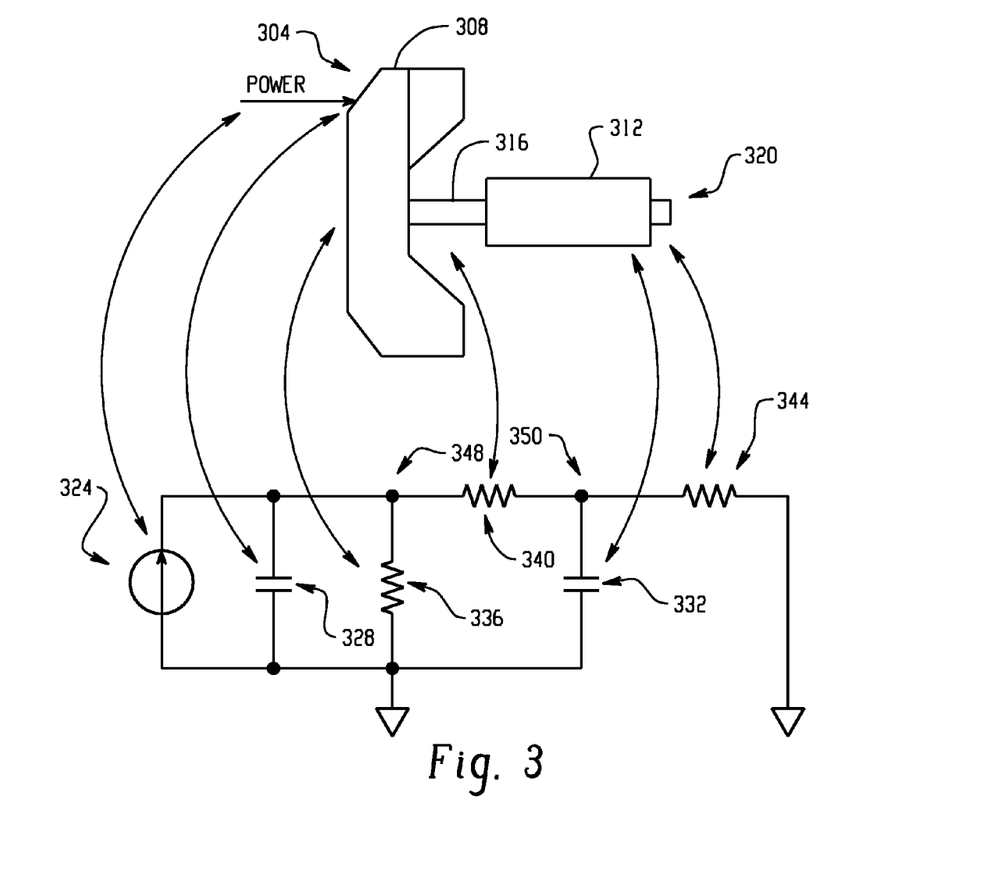
FIG. 3 illustrates an electrical circuit schematic modeling the thermal components of an x-ray source.

As noted above, the interaction between the accelerated electrons and the anode produces heat. A fraction of this heat dissipates from an anode target 304 of the anode 308 by radiation cooling. Another fraction of this heat dissipates by transferring to other components of the x-ray source 112. For example, some of the heat is transferred to bearing 312 via a stem 316 disposed between and thermally operative to an anode 308 and the bearings 312, and the transferred heat dissipates from the bearing 312 by convection cooling to cooling fluid 320. It is to be understood that the x-ray source 112 may include other components that absorb and dissipate heat.

The thermal relationship of the x-ray source components can be variously modeled, for example, as an electrical circuit as shown in FIG. 3. In FIG. 3, the power applied (joules/second) to the anode target 304 is analogous to a current source 324; heat capacity (joules/kelvin) of the anode target 304 and the bearing 312 are respectively analogous to capacitors 328 and 332; thermal resistance (kelvin*seconds/joules) of the anode 304, the stem 316, and the cooling fluid 320 are respectively analogous to resistors 336, 340, and 344; and the temperature (kelvins) of the anode target 304 and the bearing 312 are analogous to voltages 348 and 350.

Such a model can be represented in State Matrix form as expressed in equations 1 and 2:

$$d(x_d)/dt = [A]x + [B]u; \text{ and} \quad \text{Equation 1:}$$

$$y_e = [C]x_d, \quad \text{Equation 2:}$$

wherein A, B and C are matrices that include thermal properties such as heat capacity and thermal resistance parameters for the x-ray source components, x is a vector that includes x-ray source state variables such as past temperatures of the x-ray source components, u is a vector that includes input variables such as the applied power to the x-ray source 112, $x_d$ represents the determined temperature of the components, and $y_e$ represents the estimated z axis position of the focal spot.

A State Space representation of this model can be expressed as shown in equations 3 and 4:

$$\begin{bmatrix} \frac{d}{dt}TT \\ \frac{d}{dt}TB \end{bmatrix} := \begin{bmatrix} \frac{1}{HC_{Target}}\left(\frac{1}{R_{Stem}} - \frac{1}{R_{Anode}}\right) & \frac{-1}{HC_{Target} * R_{Stem}} \\ \frac{1}{HC_{Bearing} * R_{Stem}} & \frac{-1}{HC_{Bearing}}\left(\frac{1}{R_{Stem}} + \frac{1}{R_{Oil}}\right) \end{bmatrix} \begin{bmatrix} TT \\ TB \end{bmatrix} + \begin{bmatrix} \frac{1}{HC_{Target}} \\ 0 \end{bmatrix} P;$$

Equation 3 and $$Z := (K1 \ K2)\begin{bmatrix} TT \\ TB \end{bmatrix},$$

Equation 4 wherein TT represents the anode target temperature, TB represents the bearing temperature, $HC_{Target}$ represents the heat capacity of anode target 304, $HC_{Bearing}$ represents the heat capacity of bearing 312, $R_{Anode}$ represents the radiation component from anode target 304, $R_{Stem}$ represents the thermal resistance of the stem 316, $R_{Oil}$ represents the thermal resistance of the cooling liquid 320, P represents the applied power, K1 represents the coefficient of thermal expansion of the anode 308, K2 represents the coefficient of thermal expansion of the bearing 312, and Z represents the z-axis position of the focal spot.

For sake of brevity, the model shown in FIG. 3 and expressed in Equations 1-4 is in terms of the anode target 304, the stem 316, the bearing 312, and the cooling liquid 320. However, it is to be understood that such a relationship can include additional or alternative x-ray source components. For example, the housing enclosing these components and/or other structure can be included in the model.

Figure 4:
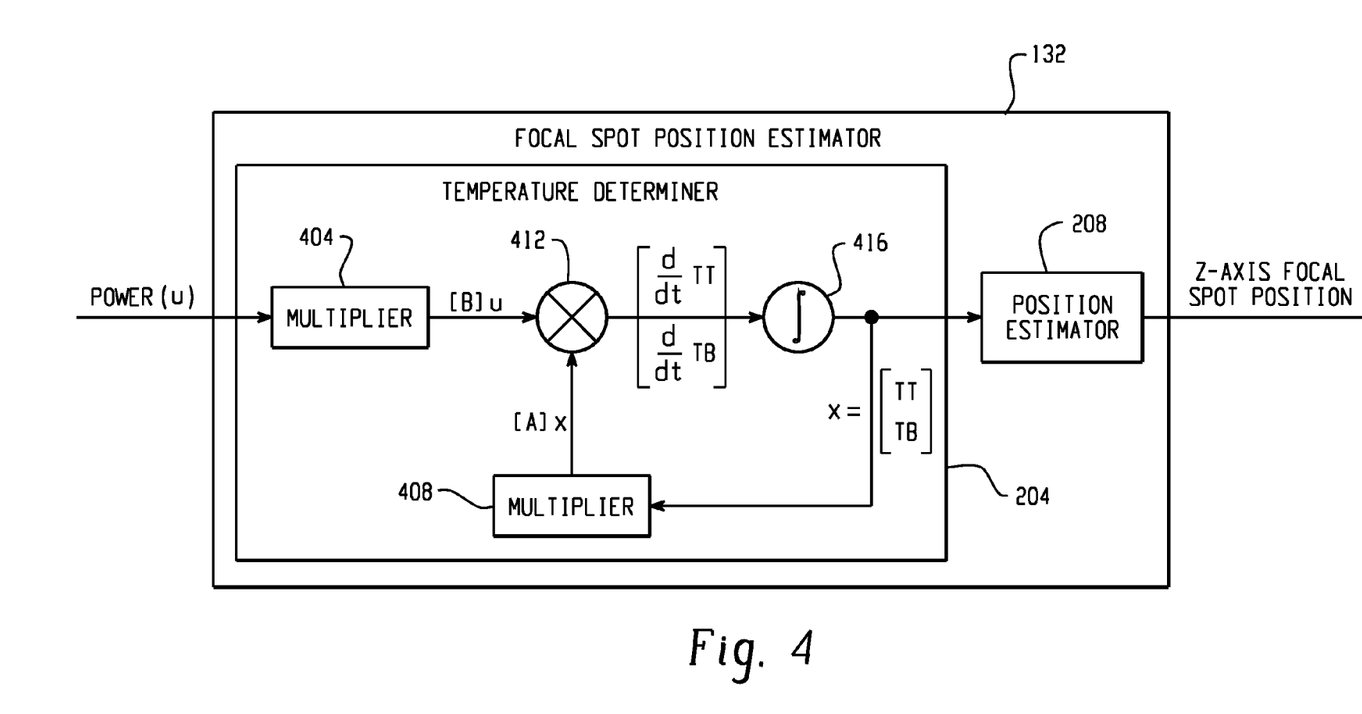
FIG. 4 illustrates a focal spot position estimator.

FIG. 4 shows an implementation of the focal spot position estimator 132 based on the above State Space representation. In this implementation, the temperature determiner 204 includes first and second multipliers 404 and 408 that respectively determine the [B]u and [A]x components of Equations 1 and 3.

The first multiplier 404 receives the variable u, which represents the applied power, and multiples u by the matrix [B], which includes a coefficient that represents the heat capacity of the anode target 304. While the scanner is not performing a scan, the variable u is zero, a null value, or the like.

The second multiplier 408 multiples the matrix [A], which includes coefficients that represents the heat capacities of the anode target 304 and the bearing 312 and the thermal resistances of the anode target 304, the stem 316, the bearing 312, and the cooling fluid 320, by previously determined temperature states of the anode target 304 and the bearing 312.

An adder 412 adds the [A]x and [B]u components to determine d/dt(TT) and d/dt(TB), and an integrator 416 integrates this result to determine x, or the anode target temperature (TT) and the bearing temperature (TB). The position estimator 208 multiples the matrix [C], which includes coefficients of thermal expansion of the anode target 304 (K1) and the bearing 312 (K2), by the determined temperatures (x) to dynamically compute the estimated z-axis position of the focal spot (Z). The determined temperatures are also fed back to the multiplier 408 and used to determine a next temperature state of the anode target 304 and the bearing 312.

Figure 5:
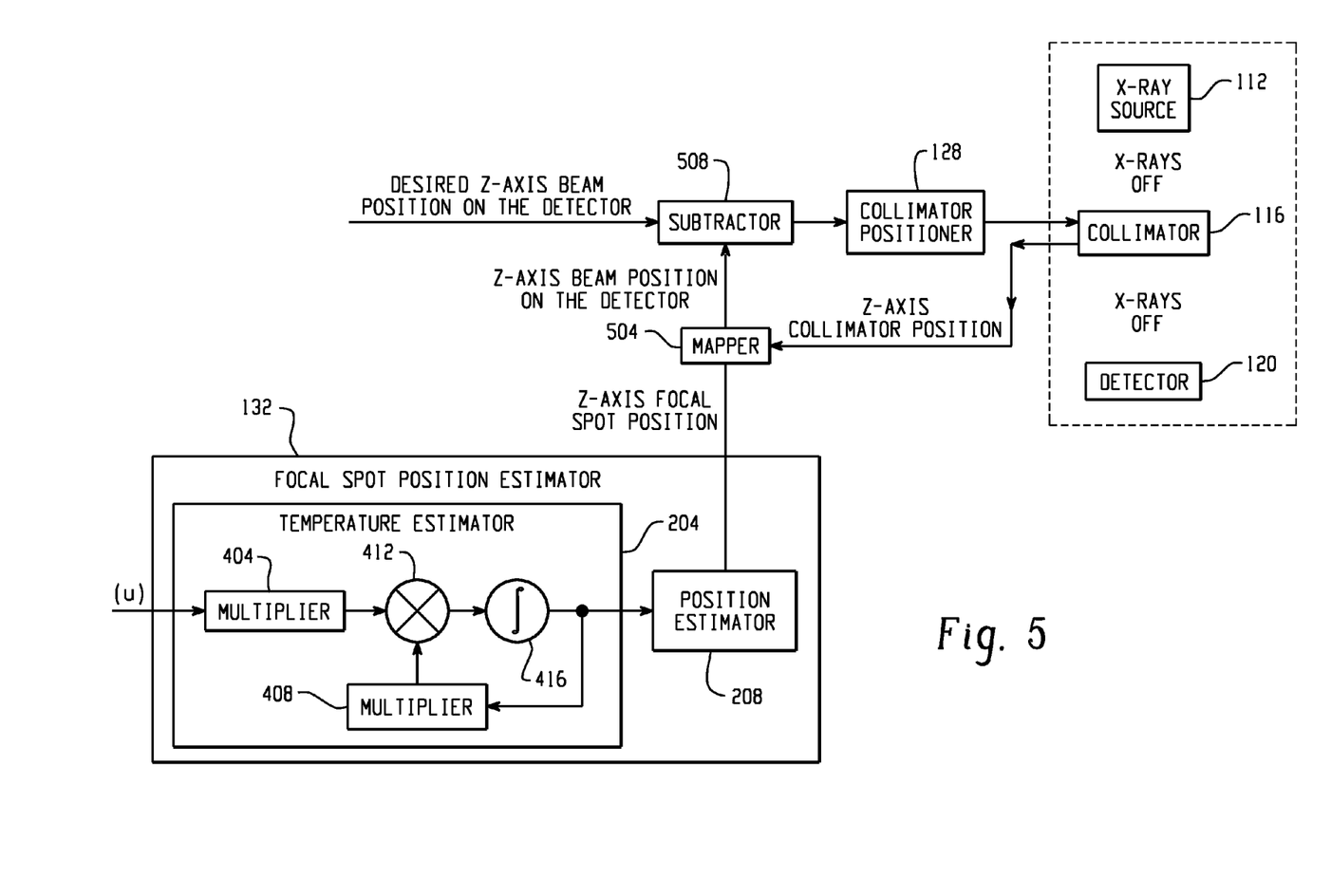
FIG. 5 illustrates a block diagram for positioning the collimator prior to performing a scan.

FIG. 5 is a block diagram illustrating an approach for using the estimator 132 of FIG. 4 to position the collimator along the z-axis prior to performing a scan. The estimator 132 dynamically computers an estimated temperature as described above.

A mapper 504 uses the estimated z-axis focal spot position and a measured z-axis collimator position to determine a z-axis position of the radiation beam on the detector 120. In this embodiment, the z-axis collimator position is determined from radiation detected with detector elements that are positioned along a transverse axis (which is generally perpendicular to the z-axis) and outside of the region used to detect radiation that traverses a patient or other object in the examination region 108.

A subtractor 508 determines a difference between this z-axis beam position and a desired z-axis beam position on the detector 120. The difference represents an error or deviation from the desired position. The difference is used by the collimator positioner 128 to position the collimator along the z-axis in accordance with the desired z-axis position. In the illustrated embodiment, it is desired to center the radiation beam about the z-axis width of the detector 120.

Figure 6:
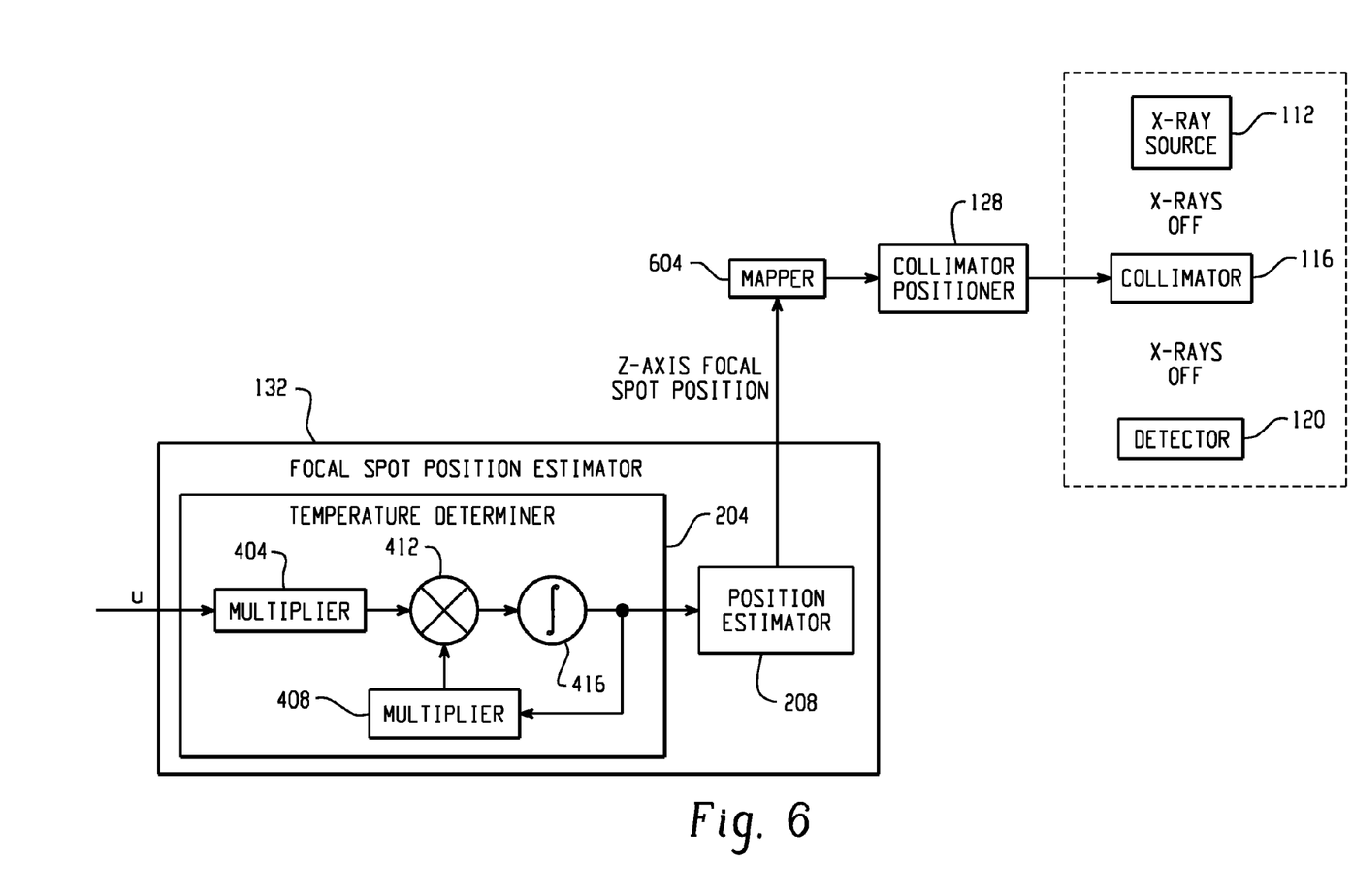
FIG. 6 illustrates a block diagram for positioning the collimator prior to performing a scan.

FIG. 6 is a block diagram illustrating another approach for using the estimator 132 of FIG. 4 to position the collimator along the z-axis prior to performing a scan. With this approach, a mapper 604 determines a desired z-axis collimator position based on the estimated z-axis focal spot position, and the collimator positioner 128 uses the desired collimator position to accordingly position the collimator 116.

Figure 7:
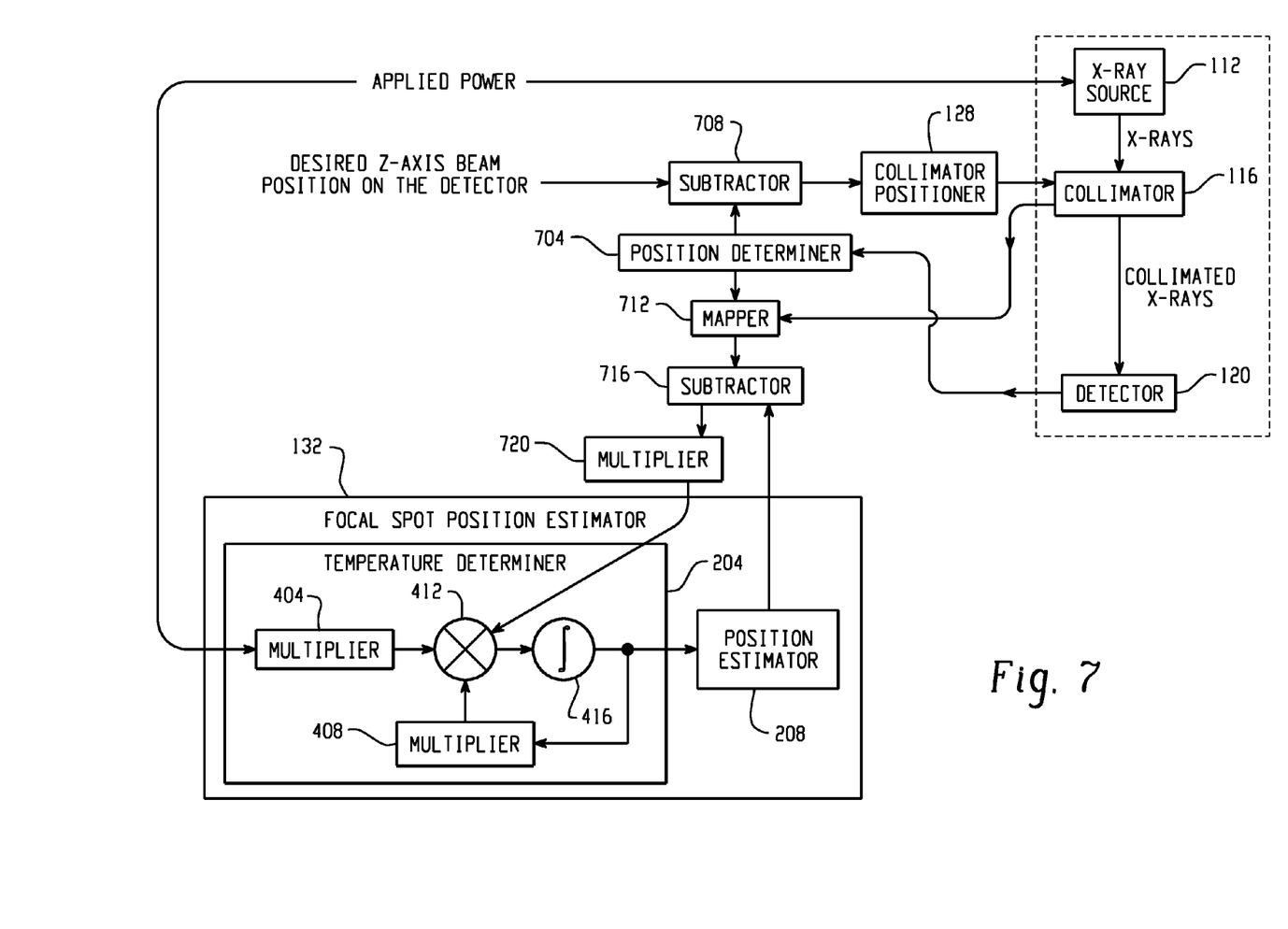
FIG. 7 illustrates a block diagram for updating the focal spot position estimator.

FIG. 7 is a block diagram illustrating an approach for positioning the collimator 116 and updating the estimator 132 while performing a scan. While scanning, a position determiner 704 determines a z-axis position of the radiation beam on the detector 120 based on detected radiation and. A subtractor 708 determines a difference between this z-axis position and a desired z-axis position of the radiation beam on the detector 120. Similar to FIG. 5, the difference represents a deviation from the desired position and is employed by the collimator positioner 128 to position the collimator 116 along the z-axis in accordance with the desired position. In the illustrated embodiment, a closed loop feedback technique is used to position the collimator 116 once per revolution of the x-ray source 112, every one (1) to five (5) seconds, or as otherwise desired.

The z-axis position of the radiation beam on the detector 120 is also used to update the estimator 132. As shown, a mapper 712 determines a z-axis position of the focal spot based on the z-axis position of the radiation beam on the detector 120. A substractor 716 determines a difference between the measured z-axis position of the focal spot and the estimated z-axis position of the focal spot. A multiplier 720 determines the product of this difference by thermal coefficients relating to the one or more x-ray source components, and the results are provided to the adder 416 of the temperature determiner 204. As a result, the output of the adder 416 includes an additional error compensation component as shown in Equation 5:

$$d(x_d)/dt = [A]x + [B]u + [G](w);$$

wherein G is a matrix of error correction coefficients and z is the difference between w-axis focal spot position and the estimated z-axis focal spot position.

In the illustrated embodiment, the estimator 132 continuously runs so that it is continuously updated with a measured z-axis focal spot position. However, the estimator 132 does not have to continuously run. In other embodiments, the estimator 132 periodically, intermittently, or otherwise is updated with the measured z-axis focal spot position. Updating the estimator 132 as such may mitigate error from accumulating between the focal spot position and the estimated focal spot position.

Figure 8:
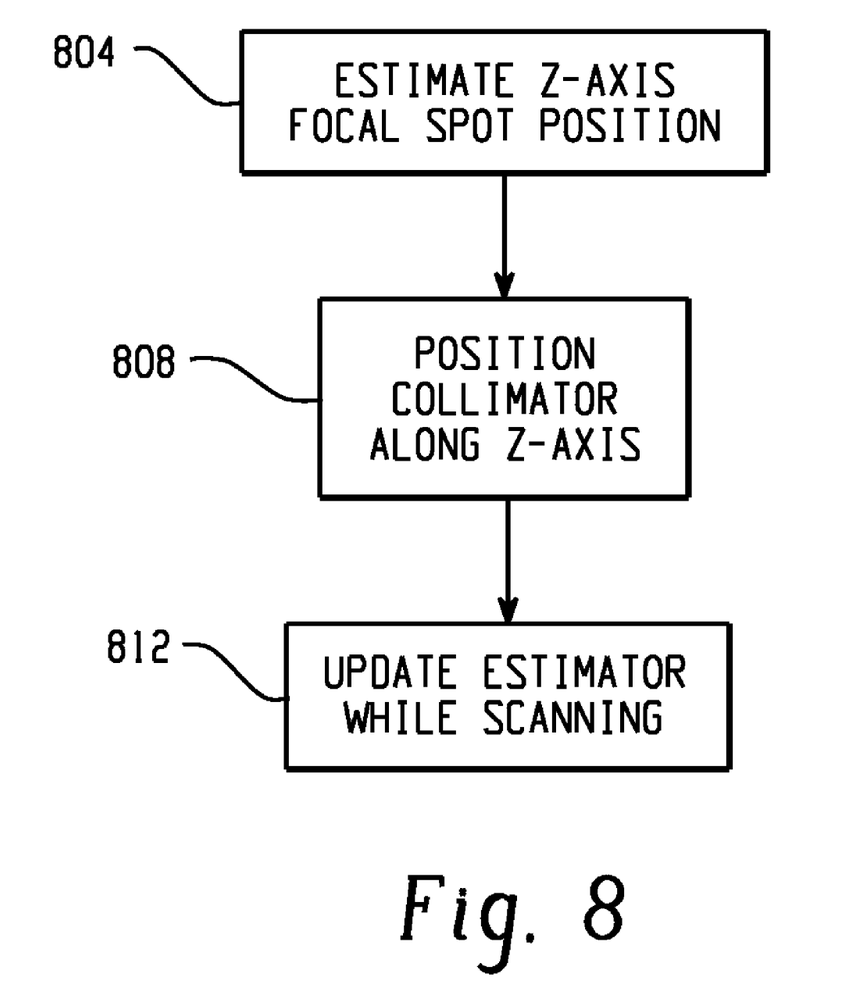
FIG. 8 illustrates a method.

FIG. 8 illustrates a method for positioning the collimator 116 along the z-axis. Assuming a scan is not being performed, at reference numeral 804 a z-axis focal spot position is estimated based on a previously determined temperature of one or more components of the x-ray source 112 in thermal communication with the anode of the x-ray source 112. At 808, the z-axis focal spot position is processed, and the collimator 116 is positioned along the z-axis based on the resulting data with respect to the focal spot and the detector 120. At 812, the estimator 132 is updated during scanning with a measured focal spot position to mitigate error in the estimated focal spot position. These steps can be repeated for each subsequent scan.

Variations are now described.

As described above, the position estimator 208 uses temperatures determined by the temperature determiner 204 to estimate the z-axis focal spot position. It is to be appreciated that the position estimator 208 may alternatively use a known, measured, or approximated temperature. For example, room temperature may be used where the scanner has not generated x-rays for some threshold period of time. In another example, the temperature of the x-ray source components may be measured using a temperature probe, a thermocouple, or an Infrared radiation detector. In yet another example, the temperature may be approximated based on a known temperature state and a cooling time constant of the x-ray source 112 via a look up table or otherwise. Determining the temperature as such may be used where the temperature determiner 204 is omitted, to determine initial temperature conditions, and/or otherwise.

In the illustrated embodiments, the z-axis focal position is used to position the collimator 116 along the z-axis. In other embodiments, the z-axis focal position may be used to additionally or alternatively position the x-ray source 112 via a source positioner, the detector 120 via a detector positioner, the focal spot via a focal spots positioner or some combination thereof. By way of example, the estimated z-axis focal spot position may be used in conjunction with a beam steering component of the cathode to steer the electron beam to a target region on the anode that will provide a radiation beam that illuminate the detector 120 as desired.

Before a scan begins, the z-axis focal position may also be used to predict where the radiation beam will be when the scan begins. In addition, since a current thermal state of the x-ray source is used to determine a next thermal state that is used to estimate the z-axis focal position, the estimated z-axis focal position may be considered a predicted z-axis focal position.

As illustrated herein, radiation detected by the detector 120 is used to determine the z-axis position of the radiation beam along the detector 120, and this position is processed to determine an error signal that is used to position the collimator 116. In an alternative embodiment, a detector located in the x-ray source or elsewhere may be used to determine the z-axis position of the radiation beam.

The focal spot estimator 132 (and, thus, the components therein) may be implemented by way of computer readable instructions which, when executed by a computer processor(s), cause the computer processor(s) to carry out the described techniques. In such a case, the instructions are stored in a computer readable storage medium associated with or otherwise accessible to the relevant computer. Likewise, any or all of the collimator positioner 128, the mapper 504, the subtractor 508, the mapper 604, the position determiner 704, the subtractor 708, the mapper 712, the subtractor 716, and the multiplier 720, may be implemented via computer readable instructions.

Applications of the forgoing and variations thereof include, but are not limited to, other imaging modalities and/or applications in which it is desirable to selectively position a radiation beam with respect to a detector.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof

Having thus described the preferred embodiments, the invention claimed is now claimed to be:

1. A medical imaging system, comprising:
   an x-ray source having a focal spot that emits radiation that traverses an examination region, wherein a position of the focal spot along a longitudinal direction is a function of a temperature of one or more x-ray source components;
   a detector that detects the radiation;
   a collimator disposed between the x-ray source and the examination region that collimates the radiation along the longitudinal direction;
   a focal spot position estimator that dynamically computes an estimated position of the focal spot along the longitudinal direction based on the temperature of one or more x-ray source components, wherein the estimated focal spot position is a function of the temperature and a coefficient of thermal expansion of the one or more x-ray source components; and
   a collimator positioner configured to position the collimator along the longitudinal direction based on the estimated focal spot position prior to performing a scan.

2. The system of claim 1, wherein the temperature includes a temperature of an anode target and a bearing of the x-ray source.

3. The system of claim 1, wherein the temperature is a function of power applied to the x-ray source.

4. The system of claim 1, wherein the focal spot position estimator dynamically computes the estimated focal spot position based on a model of one or more thermal properties of the one or more x-ray source components.

5. The system of claim 4, wherein first and second thermal properties include at least one of heat capacity and thermal resistance of the one or more x-ray source components.

6. The system of claim 1, wherein the temperature is determined by integrating a summation of first and second terms, wherein the first term is a product of a first thermal property of the one or more components and a previously determined temperature of the one or more components and the second term is a product of a second thermal property of the one or more components and power applied to the x-ray source.

7. The system of claim 1, wherein the estimated focal spot position is a function of a product of the temperature and the coefficient of thermal expansion of the one or more x-ray source components.

8. The system of claim 1, further including a beam steering component that steers an electron beam to a target region on an anode of the source based on the estimated focal spot position.

9. The system of claim 1, further including a source positioner that moves the x-ray source based on the estimated focal spot position.

10. The system of claim 1, wherein the focal spot position estimator uses the estimated focal spot position to compute a next estimated focal spot position.

11. The system of claim 1, wherein the focal spot estimator includes:
a multiplier that respectively multiplies a thermal property coefficient for the one or more x-ray source components by a previously determined temperature of the one or more x-ray source components and outputs a signal indicative thereof; and
an integrator that integrates the signal to determine the temperature of the one or more x-ray source components.

12. The system of claim 1, further including:
a mapper that maps the estimated focal spot position to a position of the radiation on the detector along the longitudinal direction based on a position of the collimator; and
a subtractor that determines a difference between the position of the radiation on the detector and a desired position of the radiation on the detector, wherein the difference is used by the collimator positioner to position the collimator.

13. The system of claim 1, further including:
a mapper that maps the estimated focal spot position to an estimated collimator position, wherein the collimator positioner employs the estimated collimator position to position the collimator.

14. The system of claim 1, wherein the focal spot position estimator receives a signal indicative of power applied to the x-ray source when the x-ray source is performing a scan, wherein the focal spot position estimator includes:
a first multiplier that respectively multiples a first thermal property coefficient of the one or more x-ray source components by a previous determined temperature of the one or more x-ray source components and outputs a first signal indicative thereof;
a second multiplier that respectively multiples a second thermal property coefficient of the one or more x-ray source components by the power applied to the x-ray source and outputs a second signal indicative thereof; and
an integrator that integrates a summation of the first and second signals to determine the temperature of the one or more x-ray source components.

15. The system of claim 14, further in including a third multiplier that determines a third signal indicative of an error between the estimated focal spot position and a measured focal spot prediction, wherein the integrator integrates a summation of the first, second and third signals to determine the temperature of the one or more x-ray source components.

16. The system of claim 15, further including:
a subtractor that determines the third signal by computing a difference between the estimated focal spot position and a measured focal spot position.

17. The system of claim 16, wherein the difference is multiplied by a thermal property coefficient of the one or more x-ray source components.

18. A method, comprising:
estimating a temperature of one or more components in thermal communication with an anode of an x-ray source of an imaging system;
computing an estimated z-axis position of the anode based on the temperature;
pre-positioning the collimator along the z-axis based on the estimated anode position before performing a scan;
monitoring a power applied to the x-ray source while scanning; and
updating the temperature based on the monitored applied power and a thermal property of the one or more x-ray source components.

19. The method of claim 18, further including multiplying the temperature by a coefficient of thermal expansion for the one or more x-ray source components to estimate the position of the anode.

20. The method of claim 18, further including using the estimated z-axis position to compute a next estimated z-axis position.

21. The method of claim 18, wherein the temperature includes a temperature of at least one of an anode target, a bearing, a stem, and cooling fluid of the x-ray source.

22. The method of claim 18, further including positioning one or more of the x-ray source, the detector, and a focal spot based on the estimated anode position.

23. The computer readable storage medium of claim 18, which, when executed, cause the computer to carry out the further steps of:
monitoring the power applied to the x-ray source while scanning; and
updating the temperature based on the monitored applied power and a thermal property of the one or more x-ray source components, or
wherein the estimated focal spot position is a function of a product of the temperature and a coefficient of thermal expansion of the one or more x-ray source components.

24. A computer readable storage medium containing instructions which, when executed, cause a computer to carry out the steps of:
estimating a temperature of one or more components in thermal communication with an anode of an x-ray source of an imaging system;
computing an estimated z-axis position of the anode based on the temperature; and
positioning a collimator along a longitudinal direction prior to performing a scan based on the computed estimated z-axis position,
wherein the temperature includes a temperature of at least one of an anode target, a bearing, a stem, and cooling fluid of the x-ray source.

* * * * *